United States Patent
Sakamoto et al.

(10) Patent No.: US 9,535,034 B2
(45) Date of Patent: Jan. 3, 2017

(54) ION CHROMATOGRAPH

(71) Applicant: SHIMADZU CORPORATION, Kyoto (JP)

(72) Inventors: Katsumasa Sakamoto, Kyoto (JP); Yukio Oikawa, Kyoto (JP); Shigeyoshi Horiike, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 289 days.

(21) Appl. No.: 14/363,027

(22) PCT Filed: Oct. 15, 2012

(86) PCT No.: PCT/JP2012/076637
§ 371 (c)(1),
(2) Date: Jun. 5, 2014

(87) PCT Pub. No.: WO2013/088834
PCT Pub. Date: Jun. 20, 2013

(65) Prior Publication Data
US 2014/0320146 A1 Oct. 30, 2014

(30) Foreign Application Priority Data
Dec. 16, 2011 (JP) .................. 2011-276311

(51) Int. Cl.
*G01N 27/62* (2006.01)
*G01N 30/96* (2006.01)
(Continued)

(52) U.S. Cl.
CPC .............. *G01N 27/62* (2013.01); *G01N 30/96* (2013.01); *G01N 2030/3038* (2013.01); *G01N 2030/645* (2013.01); *G01N 2030/965* (2013.01)

(58) Field of Classification Search
CPC G01N 27/62; G01N 30/96; G01N 2030/3038; G01N 2030/645; G01N 2030/965
(Continued)

(56) References Cited

U.S. PATENT DOCUMENTS 7,981,284 B2 * 7/2011 Sakamoto .............. B01D 61/44
204/632
8,425,842 B2 * 4/2013 Horiike .................. G01N 30/96
210/198.2
(Continued)

FOREIGN PATENT DOCUMENTS

EP 0 555 962 A2 8/1993
JP 63-91544 A 4/1988
(Continued)

OTHER PUBLICATIONS

International Search Report dated Dec. 25, 2012 issued in corresponding application No. PCT/JP2012/076637.

*Primary Examiner* — Michael Maskell
(74) *Attorney, Agent, or Firm* — Westerman, Hattori, Daniels & Adrian, LLP

(57) ABSTRACT

A suppressor is structured by an ion exchange section being structured by an eluate path forming member forming an eluate path and a regenerant path forming member forming a regenerant path being stacked across an ion exchange film, and a heat-conductive heat block covering the outside of the ion exchange section. A separation column, the suppressor, and an electrical conductivity meter are accommodated in a common constant temperature bath. The inside of the constant temperature bath is feedback-controlled by a temperature control section so as to be maintained at constant temperature.

6 Claims, 3 Drawing Sheets

(51) Int. Cl.
*G01N 30/30* (2006.01)
*G01N 30/64* (2006.01)

(58) Field of Classification Search
USPC .................................................. 250/281, 282
See application file for complete search history.

(56) References Cited

U.S. PATENT DOCUMENTS

2010/0284861 A1* 11/2010 Horiike .................. G01N 30/96
                                                                                        422/70
2010/0320132 A1* 12/2010 Sakamoto ............. B01D 61/44
                                                                                      210/198.2

FOREIGN PATENT DOCUMENTS

| | | |
|---|---|---|
| JP | 6-213882 A | 8/1994 |
| JP | 2000-39428 A | 2/2000 |
| JP | 2000039428 A * | 2/2000 |
| JP | 3272439 B2 | 4/2002 |
| JP | 2010-139387 A | 6/2010 |
| WO | 2009/087751 A1 | 7/2009 |
| WO | 2009/104262 A1 | 8/2009 |

* cited by examiner

ION CHROMATOGRAPH

TECHNICAL FIELD

The present invention relates to an ion chromatograph for separating and analyzing inorganic ions or organic ions in a sample solution.

BACKGROUND ART

An ion chromatograph introduces a sample into a separation column and separates the sample into component ions, and then, guides an eluate from the separation column into an electrical conductivity meter cell and detects the electrical conductivity, to thereby detect component ions. At this time, in order to reduce the electrical conductivity of the eluate by removing nontarget ions in the eluate from the separation column and to enable highly sensitive measurement, a suppressor is arranged between the separation column and a detector (see Patent Document 1).

As general suppressors, those that suppress the electrical conductivity of the eluate by a column filled with ion-exchange resin as a filler, and those that suppress the electrical conductivity of the eluate by arranging an eluate path and a regenerant path that face each other across an ion exchange film, and causing an eluate and a regenerant to flow through the paths are known. However, these suppressors have the following problems.

First, the electrical conductivity meter is very sensitive to temperature, and thus, there is a problem that an electrical conductivity signal changes even by a slight variation in the temperature of liquid that is introduced into the cell or the ambient temperature, appearing as a noise in the chromatogram.

Also, since the detection sensitivity is determined by the S/N ratio, the detection sensitivity is increased to the extent that the noise is smaller, even if the output signal of the detector with respect to the density is the same. The degree of change in the electrical conductivity by the temperature is greater as the electrical conductivity of liquid is higher. In the case of an ion chromatograph, in order to separate an ionic sample using a separation column containing ion-exchange resin, a highly ionic eluate is indispensable, and as a result, the electrical conductivity of the eluate is increased. Accordingly, although the electrical conductivity of the eluate from the column, that is, background electrical conductivity, is suppressed by the suppressor, it is not possible to completely eliminate the background electrical conductivity. Accordingly, there is a problem that, when the temperature of the suppressor changes due to a change in the ambient temperature of the suppressor, the temperature of the eluate from the suppressor also changes, and the background electrical conductivity of the eluate is changed under the influence, and the measurement accuracy is reduced.

PRIOR ART DOCUMENTS

Patent Documents

Patent Document 1: Japanese Patent No. 3272439
Patent Document 2: Japanese Patent Laid-open Publication No. 2010-139387

SUMMARY OF THE INVENTION

Problems to be Solved by the Invention

To solve the problems described above, there are applied methods of arranging a suppressor in a column oven for performing temperature control for a separation column to thereby maintain the temperature of the suppressor constant, and of keeping a suppressor and a column oven in contact with each other by a heat-transfer member to thereby maintain the temperature of the suppressor constant (see Patent Document 2). However, even when these methods are applied, it is difficult to stably perform highly sensitive analysis at several tens of ppb.

Also, there is no commercially available suppressor using an ion exchange film that is capable of performing highly sensitive measurement under the condition of high temperature.

Accordingly, the present invention has its object to stabilize the background electrical conductivity of an eluate from a separation column, and to allow highly sensitive measurement to be stably performed.

Solutions to the Problems

The present invention is an ion chromatograph including a separation path including a separation column for performing separation of an ion component in a sample, a measurement path including an electrical conductivity meter for measuring electrical conductivity, and a suppressor including an eluate path, connecting between the separation path and the measurement path, for passing an eluate from the separation column, a regenerant path, arranged facing the eluate path, for passing a regenerant, and an ion exchange film, interposed between the eluate path and the regenerant path, for causing ion exchange to be performed between the paths, the suppressor being for suppressing background electrical conductivity of the eluate from the separation column, wherein the suppressor is structured by an ion exchange section structured by an eluate path forming member forming the eluate path, the ion exchange film, and a regenerant path forming member forming the regenerant path being stacked with one another, and a heat-conductive heat block covering the ion exchange section, and wherein the electrical conductivity meter and the suppressor are accommodated in a common constant temperature bath.

Effects of the Invention

According to the present invention, a suppressor structured by an ion exchange section structured by an eluate path forming member forming an eluate path, an ion exchange film, and a regenerant path forming member forming a regenerant path being stacked with one another, and a heat-conductive heat block covering the ion exchange section is accommodated in a common constant temperature bath together with an electrical conductivity meter, and thus, the heat of the constant temperature bath may be easily transferred to the ion exchange section inside the suppressor via the heat block, and the responsiveness for temperature control for the ion exchange section is increased. Moreover, the heat capacity is increased due to the ion exchange section being covered by the heat block, compared to a case where the suppressor is structured only by the ion exchange section, and the temperature of the suppressor is less likely to change. Since the suppressor is accommodated in the constant temperature bath together with the electrical conductivity meter, an eluate is prevented from changing while being introduced into the electrical conductivity meter from the suppressor. Accordingly, the temperature of the suppressor is maintained at constant temperature with high accuracy and the temperature of an eluate from the suppressor is maintained at constant temperature, and thus, the background electrical conductivity of the eluate may be stabilized with high accuracy, and highly sensitive measurement may be stably performed.

EMBODIMENTS OF THE INVENTION

Figure 1:
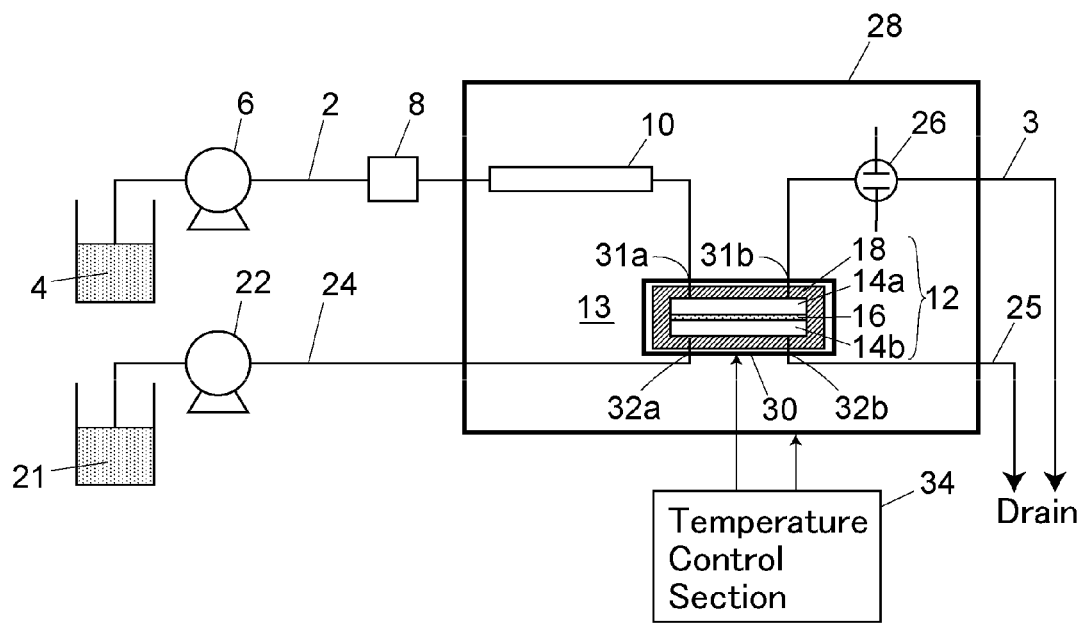
FIG. 1 is a path structure diagram schematically showing an example of an ion chromatograph.

According to a preferred embodiment of an ion chromatograph of the present invention, a suppressor temperature adjustment mechanism, attached to a suppressor, for adjusting the temperature of the suppressor to constant temperature the same as the temperature in a constant temperature bath is further included. Inside the constant temperature bath which is controlled to constant temperature, a change in the temperature of the suppressor is small, and the suppressor temperature adjustment mechanism controls the temperature of the suppressor to constant temperature based on the small change in the temperature, and thus, the accuracy of temperature control for the suppressor is increased and the temperature of the suppressor may be further stabilized.

The thickness of an ion exchange section of the suppressor in the stacking direction is preferably 2 mm or less. Then, heat from a heat block is more easily transferred to an eluate path, and the responsiveness of temperature control for an eluate flowing through the eluate path may be increased.

Incidentally, it is known that if temperature of the suppressor is raised, ion exchange rate in the suppressor is increased, and the measurement sensitivity is increased by the rise in the S/N ratio. However, if the temperature of the suppressor is made 40° C. or higher, there is a problem that impure substances in a resin member structuring the suppressor dissolve, and the impure substances enter the eluate and cause contamination.

Thus, according to a preferred embodiment of the ion chromatograph of the present invention, an eluate path forming member and a regenerant path forming member structuring the ion exchange section are formed of polyether ether ketone (PEEK) resin, and the temperature of the constant temperature bath is controlled to be 40° C. or higher and 100° C. or lower. Since impure substances do not dissolve from the PEEK resin even under a condition of high temperatures of 40° C. or higher, contamination does not occur and highly sensitive measurement may be performed. The chemical equilibration rate of diffusion dialysis is more easily stabilized due to the temperature of solution in the suppressor being constant at a high temperature, and variations in the electrical conductivity signals dependent on the solution density are improved.

An electrical conductivity meter is preferably provided integrally with the heat block. The device structure may thus be simplified. Also, the temperature of the path of an eluate from the suppressor to the electrical conductivity meter is also controlled by the heat block, and thus, the temperature of the eluate that is introduced from the suppressor into the electrical conductivity meter may be stabilized at constant temperature.

According to a preferred embodiment, the eluate path and the regenerant path of the ion exchange section are each 500 μm or less in width, 100 μm or less in depth, and 3000 mm or less in length. The flow of liquid in the eluate path and the regenerant path may thereby be easily made laminar flow, and the flow of liquid may be stabilized.

An example of the ion chromatograph will be described with reference to the drawings. First, a structure of an example of the ion chromatograph will be described with reference to FIG. 1.

The ion chromatograph of this example includes a separation path 2, a measurement path 3, a regenerant delivery path 24, and a regenerant discharge path 25. One end of each of the paths is connected to a port provided to an ion exchange unit 13. Details of the ion exchange unit 13 will be given below, but the ion exchange unit 13 is structured by a suppressor 12 and a constant temperature bath 30.

An upstream end of the separation path 2 is connected to a container 4 storing an eluent. A delivery pump 6 for delivering the eluent, a sample injection section 8 for injecting a sample into the separation path 2, and a separation column 10 for separating the sample into each component are provided on the separation path 2. A downstream end of the measurement path 3 is a drain, and an electrical conductivity meter 26 is provided on the measurement path 3.

An upstream end of the regenerant delivery path 24 is connected to a container 21 storing a regenerant. A delivery pump 22 for delivering the regenerant is provided on the regenerant solution path 24. A downstream end of the regenerant discharge path 25 is a drain.

The suppressor 12 of the ion exchange unit 13 is structured in such a way that an eluate path and a regenerant path face each other across an ion exchange film 16, and is for suppressing the electrical conductivity of the eluate by causing the eluate from the separation column 10 and the regenerant to flow through the eluate path and the regenerant path, respectively, and for stabilizing the background electrical conductivity of the eluate measured by the electrical conductivity meter 26. The ion exchange section is structured by an eluate path forming member 14a forming the eluate path and a regenerant path forming member 14b forming the regenerant path being stacked across the ion exchange film 16, and the suppressor 12 is structured by a heat-conductive heat block 18 covering the outside of the ion exchange section.

The suppressor 12 is accommodated inside the constant temperature bath 30, which is the suppressor temperature adjustment mechanism. The inside of the constant temperature bath 30 is feedback-controlled by a temperature control section 40 so as to maintain the temperature of the suppressor 12 to constant temperature of 40° C., for example.

The separation column 10, the ion exchange unit 13, and the electrical conductivity meter 26 are accommodated inside a common constant temperature bath 28. The inside of the constant temperature bath 28 is also feedback-controlled by the temperature control section 34 so as to be maintained at the same constant temperature of, for example, 40° C., as the constant temperature bath 30. Although not shown, a temperature sensor for detecting the temperature inside the constant temperature bath 28, and a temperature sensor for detecting the temperature inside the constant temperature bath 30 are provided, and the temperature control section 34 controls the output of heaters provided in the constant temperature bath 28 and the constant temperature bath 30 based on the signals from the temperature sensors.

The ion exchange unit 13 includes an eluate inlet port 31a, an eluate outlet port 31b, a regenerant inlet port 32a, and a regenerant outlet port 32b. The eluate inlet port 31a is a port that is communicated with an end of the eluate path of the suppressor 12, and a downstream end of the separation path 2 is connected thereto. The eluate outlet port 31b is a port that is communicated with the other end of the eluate path of the suppressor 12, and an upstream end of the measurement path 3 is connected thereto. The regenerant inlet port 32a is a port that is communicated with an end of the regenerant path of the suppressor 12, and a downstream end of the regenerant delivery path 24 is connected thereto. The regenerant outlet port 32b is a port that is communicated with the other end of the regenerant path of the suppressor 12, and an upstream end of the regenerant discharge path 25 is connected thereto.

Figure 2:
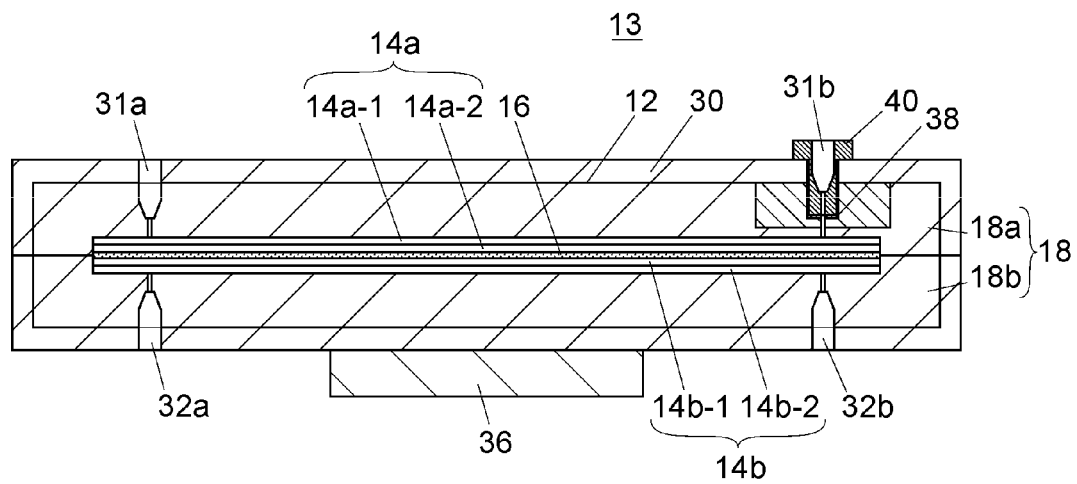
FIG. 2 is a cross-sectional diagram showing an example of a structure of an ion exchange unit.

An example of a structure of the ion exchange unit 13 will be described with reference to FIG. 2. As described above, the ion exchange unit 13 is structured by the suppressor 12 and the constant temperature bath 30. The suppressor 12 is structured by an ion exchange section formed from stacked films 14a-1, 14a-2, 16, 14b-1, and 14b-2, and a heat-conductive heat block 18 that accommodates and fixes the ion exchange section. The material of the films 14a-1, 14a-2, 14b-1, and 14b-2 is PEEK resin. The material of the heat block 18 is, for example, aluminum. The heat block 18 is structured by two members 18a and 18b, and these members 18a and 18b are fixed by fasteners formed of a bolt and a nut (not shown) while sandwiching the ion exchange section from both sides.

The constant temperature bath 30 is structured by a heat-conductive block of stainless steel or the like that is adhered to, and covers, the outer surface of the heat block 18, and a heater 36 is attached thereto. Although not shown, a temperature sensor such as a thermocouple for detecting the temperature inside the heat block 18 is attached, and the output of the heater 36 is feedback-controlled based on the detection signal of the temperature sensor.

Figure 3:
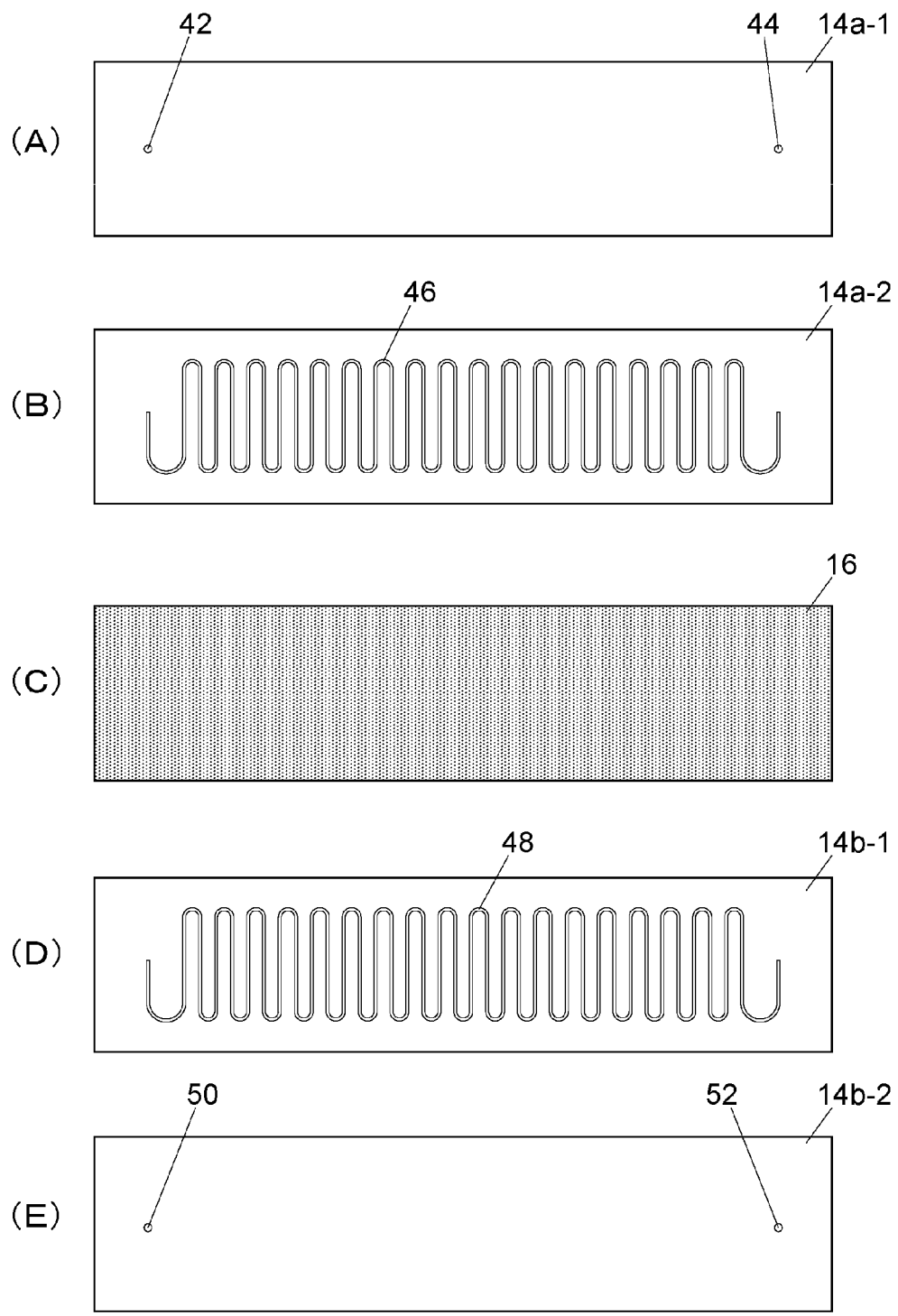
FIGS. 3(A) to 3(E) are plan views of filters for describing respective filters forming an ion exchange section.

The films 14a-1 and 14a-2 form the eluate path forming member 14a. A meandering through groove 46 to be the eluate path is formed to the film 14a-2 (see FIG. 3(B)). The through groove 46 forms the eluate path by the film 14a-2 being stacked between the film 14a-1 and the ion exchange film 16. The film 14a-1 includes through holes 42 and 44 to be paths communicated with the eluate path, at positions corresponding to the ends of the through groove 46 of the film 14a-2 (see FIG. 3(A)).

The films 14b-1 and 14b-2 form the regenerant path forming member 14b. A meandering through groove 48 to be the regenerant path is formed in the film 14b-1 (see FIG. 3(D)). The through groove 48 is formed, facing the through groove 46 across the ion exchange film 16, and has a shape that is substantially the same as that of the through groove 46. The through groove 48 forms the regenerant path by the film 14b-1 being stacked between the film 14b-2 and the ion exchange film 16. The film 14b-2 includes through holes 50 and 52 to be paths communicated with the regenerant path, at positions corresponding to the ends of the through groove 48 of the film 14b-1 (see FIG. 3(E)).

The heat block 18 and the heat-conductive block of the constant temperature bath 30 include the eluate inlet port 31a and the eluate outlet port 31b that are communicated with the through holes 42 and 44 of the film 14a-1, and the regenerant inlet port 32a and the regenerant outlet port 32b that are communicated with the through holes 50 and 52 of the film 14b-2. An electrical conductivity measurement section 38 for measuring the electrical conductivity of a solution flowing through a path connecting the through hole 44 of the film 14a-1 and the eluate outlet port 31b is provided at a portion of the heat block 18 where the eluate outlet port 31b is formed. The electrical conductivity measurement section 38 structures the electrical conductivity meter 26 in FIG. 1, and the suppressor 12 and the electrical conductivity meter 26 are integrated. The eluate outlet port 31b is provided to an adapter 34 that is mounted to a hole that is provided at a portion where the electrical conductivity measurement section 38 is formed.

Figure 4:
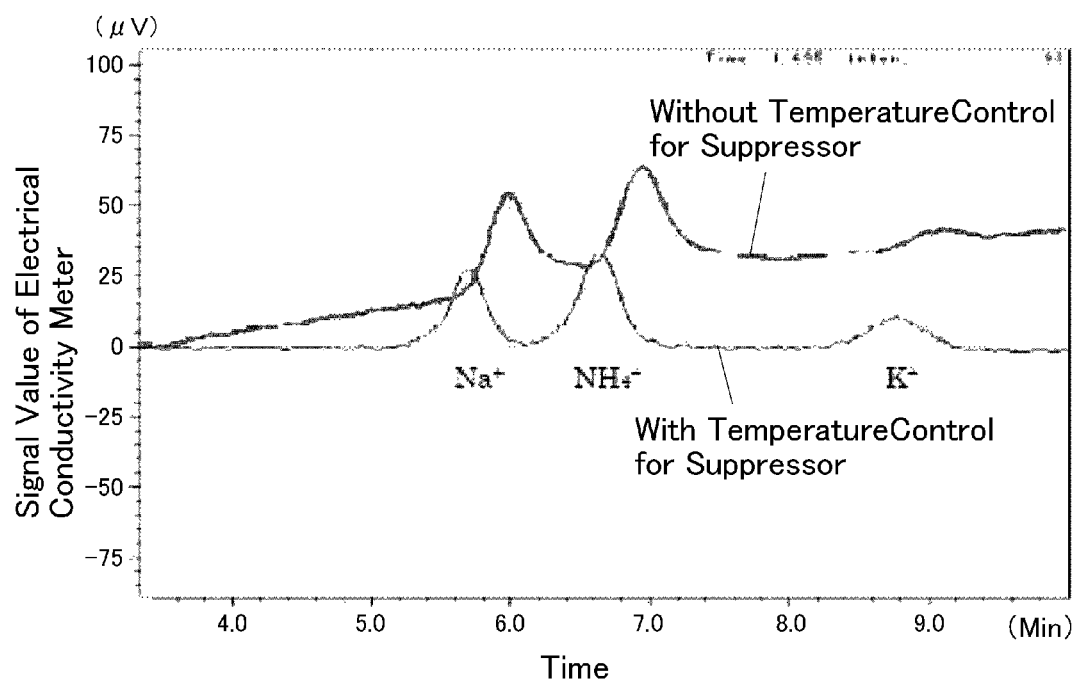
FIG. 4 is a graph showing signals of an electrical conductivity meter of cases where temperature control for a suppressor is performed and where the temperature control is not performed.

According to the structure described above, the temperature control for the inside of the suppressor 12 may be performed with the accuracy of ±0.02° C. By stabilizing the temperature control for the suppressor 12 at the relatively high temperature of 40° C., the signal of the electrical conductivity meter 26 is prevented from drifting and the baseline is stabilized, compared to a case where temperature control for the suppressor 12 is not performed, as shown in FIG. 4. Accordingly, detection of a low peak such as the peak of $K^+$ ion in the drawing is facilitated, and the detection sensitivity is increased.

Additionally, in the example described above, the suppressor 12 is accommodated inside the constant temperature bath 30, but this structure is not essential. The electrical conductivity signal of the electrical conductivity meter 26 may also be stabilized by a structure according to which the suppressor 12 in which the ion exchange section is covered by the heat block 18 is accommodated inside the constant temperature bath 28 together with the electrical conductivity meter 26. The heat capacity of the suppressor 12 is increased due to the structure of the suppressor 12 where the ion exchange section is covered by the heat block 18, and thus, even if the temperature of a solution entering the suppressor 12 changes, the temperature of the suppressor 12 is unlikely to change. Thus, even if the temperature outside the constant temperature bath 28 changes, and the temperature of the eluate changes, the temperature of the eluate introduced into the electrical conductivity meter 26 and the ion exchange rate in the suppressor 12 are not greatly affected, and variation in the background electrical conductivity is suppressed.

DESCRIPTION OF REFERENCE SIGNS

2: Separation path
3: Measurement path
4: Eluent storage container
6, 22: Delivery pump
8: Sample injection section
10: Separation column
12: Suppressor
13: Ion exchange unit
14a: Eluate path forming member
14b: Regenerant path forming member
16: Ion exchange film
18: Heat block
21: Regenerant storage container
24: Regenerant delivery path
25: Eluate discharge path
26: Electrical conductivity meter
28, 30: Constant temperature bath
31a: Eluate inlet port
31b: Eluate outlet port
32a: Regenerant inlet port
32b: Regenerant outlet port 34: Temperature control section
36: Heater
38: Electrical conductivity measurement section
40: Adapter

The invention claimed is:

1. An ion chromatograph comprising:
a separation path including a separation column for performing separation of an ion component in a sample;
a measurement path including an electrical conductivity meter for measuring electrical conductivity; and
a suppressor including an eluate path, connecting between the separation path and the measurement path, for passing an eluate from the separation column, a regenerant path, arranged facing the eluate path, for passing a regenerant, and an ion exchange film, interposed between the eluate path and the regenerant path, for causing ion exchange to be performed between the paths, the suppressor being for suppressing background electrical conductivity of the eluate from the separation column,
wherein the suppressor is structured by an ion exchange section structured by an eluate path forming member forming the eluate path, the ion exchange film, and a regenerant path forming member forming the regenerant path being stacked with one another, and a heat-conductive heat block covering the ion exchange section,
wherein the electrical conductivity meter and the suppressor are accommodated in a common constant temperature bath, and
wherein the ion chromatograph further comprising a suppressor temperature adjustment mechanism, having a heater to heat the suppressor, attached to the suppressor and accommodated in the common constant temperature bath, for adjusting temperature of the suppressor to constant temperature same as temperature in the constant temperature bath.

2. The ion chromatograph according to claim 1, wherein a thickness of the ion exchange section in a stacking direction is 2 mm or less.

3. The ion chromatograph according to claim 1, wherein the eluate path forming member and the regenerant path forming member are formed of polyether ether ketone resin, and the temperature in the constant temperature bath is controlled to constant temperature of 40° C. or higher and 100° C. or lower.

4. The ion chromatograph according to claim 1, wherein the electrical conductivity meter is provided integrally with the heat block.

5. The ion chromatograph according to claim 1, wherein the eluate path and the regenerant path are each 500 μm or less in width, 100 μm or less in depth, and 3000 mm or less in length.

6. The ion chromatograph according to claim 1, wherein the constant temperature bath is adhered to, and covers, outer surface of the heat block.

* * * * *